United States Patent [19]

Kim et al.

[11] Patent Number: 4,902,845

[45] Date of Patent: Feb. 20, 1990

[54] METHOD TO EXTEND LIFE OF IRON OXIDE-CONTAINING CATALYSTS USING LOW LEVELS OF OXYGEN

[75] Inventors: Dae K. Kim; George A. McConaghy, both of Naperville, Ill.

[73] Assignee: Amoco Corporation, Chicago, Ill.

[21] Appl. No.: 274,444

[22] Filed: Nov. 21, 1988

Related U.S. Application Data

[63] Continuation of Ser. No. 345,663, Feb. 4, 1982, abandoned.

[51] Int. Cl.$^4$ .................. C07C 4/18; C07C 5/333; C07C 15/46; B01J 23/94
[52] U.S. Cl. ........................ 585/486; 423/362; 502/30; 502/52; 518/719; 585/443; 585/444; 585/445; 585/487; 585/531; 585/629; 585/630
[58] Field of Search .................. 585/486, 487; 502/30, 502/51, 52

[56] References Cited

U.S. PATENT DOCUMENTS

| | | | |
|---|---|---|---|
| 2,401,846 | 6/1946 | Sumerford | 585/44 |
| 2,541,680 | 2/1951 | Vesterdal | 502/55 |
| 2,848,521 | 8/1958 | Polk | 502/52 |
| 3,485,882 | 12/1969 | Hess et al. | 585/487 |
| 3,502,737 | 3/1970 | Ghublikiah | 585/444 |
| 3,654,181 | 4/1972 | Sutherland Jr. et al. | 502/55 |
| 4,260,518 | 4/1981 | Katzer et al. | 502/517 |

FOREIGN PATENT DOCUMENTS

959854  6/1964  United Kingdom ................ 585/487

*Primary Examiner*—Paul E. Konopka
*Attorney, Agent, or Firm*—Wallace L. Oliver; William H. Magidson; Ralph C. Medhurst

[57] ABSTRACT

Catalyst activity life of an iron oxide-containing catalyst is extended by contacting such catalyst with a feedstream containing about 0.0001 to about 0.01 mole of oxygen per mole of feed in the substantial absence of an oxidation catalyst.

2 Claims, 2 Drawing Sheets

METHOD TO EXTEND LIFE OF IRON OXIDE-CONTAINING CATALYSTS USING LOW LEVELS OF OXYGEN

This is a continuation of application Ser. No. 345,663, filed Feb. 4, 1982, now abandoned.

BACKGROUND OF THE INVENTION

This invention relates to hydrocarbon conversion processes using an iron oxide catalyst and more particularly relates to extending iron oxide-containing catalyst life in alkyl aromatic dehydrogenation processes.

Iron oxide catalysts have been used widely in various conversion processes including dehydrogenation and hydrocarbon synthesis. Examples of these processes include dehydrogenation such as ethylbenzene to styrene, ethyltoluene to vinyltoluene and butenes to butadiene; formation of gasoline fraction hydrocarbons from synthesis gas (hydrogen and carbon monoxide) as in the Fischer-Tropsch process; dealkylation of alkylaromatics such as toluene to benzene and synthesis of ammonia from nitrogen and hydrogen As in most heterogeneous catalytic systems, an iron oxide catalyst typically declines in conversion activity over time. A process that could extend the useful life of an iron oxide catalyst would be very advantageous. The process of this invention contacts molecular oxygen over an iron oxide catalyst at very low concentrations which surprisingly prolongs catalyst life. The use of oxygen in hydrocarbon conversion processes with an iron oxide catalyst has been reported in several U.S. patents. However, the concentrations of oxygen used therein are either substantially greater than the effective range demonstrated in this invention or are used in conjunction with an oxidation catalyst to provide process heat. Generally, use of oxygen in such patents was for a different purpose than prolonging catalyst life as discovered in this invention.

U.S. Pat. No. 3,437,703 describes a process to dehydrogenate ethylbenzene to styrene over a catalyst containing an iron oxide component and an oxidation catalyst component in the presence of oxygen (0.01 to 10 mole percent of total process stream). The oxygen is used in conjunction with the oxidation catalyst (typically salts of platinum and palladium) to "burn" hydrogen formed in the dehydrogenation process to provide heat necessary to drive the endothermic dehydrogenation reaction and to remove gaseous hydrogen from the reaction system which thermodynamically favors styrene production. U.S. Pat. No. 3,855,330 likewise describes adding oxygen to an ethylbenzene dehydrogenation process using an oxidation catalyst together with an iron oxide dehydrogenation catalyst. Again the oxygen is used to oxidize hydrogen or carbon-containing materials to provide process heat. This patent discloses oxidizing and dehydrogenating in separate zones and teaches that, although oxygen is present in the oxidation zone, less than 0.01 mole of oxygen per mole of ethylbenzene is permitted in the dehydrogenation zone and preferably there is a practically complete absence of oxygen in the gases leaving the oxidation zone.

U.S. Pat. No. 3,502,737 discloses incorporating oxygen in an ethylbenzene dehydrogenation process at levels of 0.01 to 1.0 moles of oxygen per mole of ethylbenzene to burn carbon and hydrogen to produce process heat which reduces steam requirements. The data contained in this patent show that styrene yield generally declines as the oxygen content increases.

U.S. Pat. No. 2,945,900 discloses using oxygen at 5 to 40 vol.% levels in a dehydrogenation process using calcium nickel phosphorus-type atalyst. Processes using oxygen with an iron oxide catalyst are excluded specifically in this patent.

U.S. Pat. No. 4,039,601 describes a method to regenerate a coked iron oxide catalyst with oxygen and steam by continuously removing catalyst from a reactor, regenerating such removed catalyst outside the reactor and returning the regenerated catalyst to the reactor.

Another process using oxygen in an ethylbenzene dehydrogenation reacts about 0.5 mole of oxygen together with steam and an inert gas with ethylbenzene to form styrene and water over various catalysts including iron oxide. Such oxidative dehydrogenation operates at low temperature and typically results in poor yield with substantial carbon oxide formation.

U.S. Pat. No. 3,505,422 describes adding carbon dioxide to a feedstream of steam in a dehydrogenation process using an iron oxide catalyst to reduce the amounts of undesirable by-products.

SUMMARY OF THE INVENTION

Catalytic activity life of an iron oxide-containing catalyst is extended by contacting such catalyst with a feed stream containing about 0.0001 to about 0.01 mole of oxygen per mole of feed in the substantial absence of an oxidation catalyst.

BRIEF DESCRIPTION OF THE INVENTION

Figure 1:
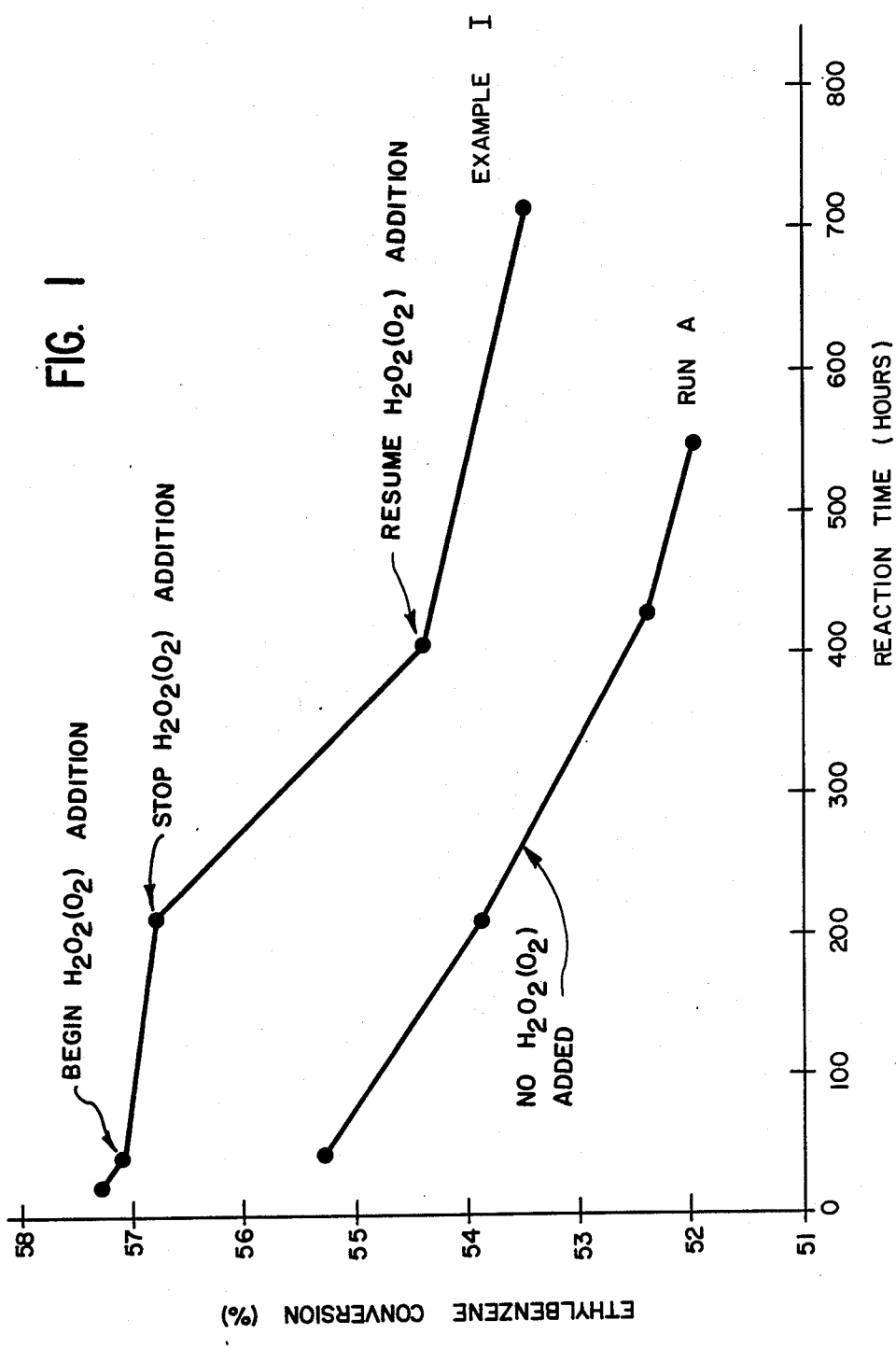
FIG. 1 illustrates data from Example I and Comparative Run A showing the effect of hydrogen peroxide addition to process steam on ethylbenzene conversion as a function of time.

The invention described herein is a method to extend catalyst life in an iron oxide catalyst system using low levels of molecular oxygen. In one aspect of this invention low levels of molecular oxygen are contacted with an iron oxide catalyst system useful in dehydrogenating ethylbenzene to styrene. The hydrocarbon conversion reactions in which the method of this invention can be useful include conversion of light hydrocarbons such as butane dehydrogenation, conversion of synthesis gas to liquid hydrocarbons and dealkylating alkyl aromatics such as demethylating toluene to benzene. Another conversion reaction in which the process of this invention can be useful is producing ammonia from hydrogen and nitrogen at high pressure.

Accordingly, reactant feeds which can be contacted with an iron oxide-containing catalyst in a conversion process include aliphatic hydrocarbons such as alkanes and alkenes, aromatic hydrocarbons such as ethylbenzene, toluene and cumene, synthesis gas, and a mixture of nitrogen and hydrogen. Other specific examples of aliphatic hydrocarbons include butane, butene-1, butene-2, pentene and other $C_4$-$C_{20}$ linear or branched alkanes or alkenes. Other examples of aromatic hydrocarbons include alkyl-substituted benzenes having one or more $C_1$-$C_{10}$ alkyl groups.

Dehydrogenation of ethylbenzene to styrene over an iron oxide catalyst system provides a useful illustration of the method of this invention. Dehydrogenation of ethylbenzene to styrene typically is accomplished commercially with an iron oxide catalyst promoted with potassium compounds in the presence of excess superheated steam. The steam supplies heat required for the endothermic reaction while maintaining a suitable reaction temperature and further acts as a diluent which thermodynamically favors the conversion reaction. In addition, steam removes coke deposited on the catalyst which prolongs catalyst life. The steam/hydrocarbon ratio used in dehydrogenation processes usually can range from about 5 to above 15 and typically is about 10 to 15 moles of steam per mole of hydrocarbon feed. Energy costs in such dehydrogenation processes can be reduced to some extent by increasing catalyst selectivity, i.e., decreasing byproduct formation, or by reducing steam usage. However, it has been found that reduction of steam usage by lowering the steam/hydrocarbon mole ratio typically below about 10–12 decreases catalyst life, and that, generally, highly selective catalysts are less active than conventional catalysts and require substantially higher reaction temperatures and steam/hydrocarbon mole ratios typically above about 10–12 in order to maintain catalyst performance and life.

Catalyst life can be extended according to the method of this invention by contacting a catalyst incorporating iron oxide with a reactant feedstream, typically a hydrocarbon feedstream, containing about 0.0001 to 0.01, preferably about 0.0005 to about 0.007, moles of oxygen per mole of such feed. Use of such low levels of oxygen does not materially affect hydrocarbon selectivities. Thus, according to this invention oxygen can be fed continuously into a hydrocarbon conversion process and is distinct from a process in which oxygen is used periodically to burn off coke from a heterogeneous catalyst.

Introduction of oxygen gas as pure oxygen or diluted, as in air, is not the only method by which molecular oxygen can be contacted at low levels with an iron oxide-containing catalyst according to this invention. Peroxides compatible with the hydrocarbon conversion process, such as hydrogen peroxide, can be incorporated in a feedstream which will convert to molecular oxygen in situ and will be in contact with the catalyst. Such peroxides are considered oxygen precursors according to this invention.

Molecular oxygen or a precursor species can be introduced in any convenient manner to the hydrocarbon conversion process such that oxygen contacts the iron oxide-containing catalyst. For example, oxygen or a precursor can be incorporated with a hydrocarbon feedstream, recycle loop or steam input. In dehydrogenation of ethylbenzene to styrene, oxygen or a precursor such as hydrogen peroxide typically is added to an input line directly before contact with the catalyst. If there is more than one catalyst-containing reactor, oxygen or a precursor can be added to each such reactor.

Catalysts useful in this invention are those containing an oxide of iron. Preferably, a substantial portion of such iron oxide is in the form $Fe_3O_4$, although $Fe_2O_3$ may be reduced in situ by hydrogen to $Fe_3O_4$. Usually, further reduction to FeO leads to an inactive catalyst species. Other materials can be present in minor amounts as promoters or stabilizers. Examples of such added materials are nonoxidation catalytic compounds of Groups IA, IB, IIA, IIB, IIIA, VB, VIB, VIIB and VIII and rare earths, such as zinc oxide, magnesium oxide, chromium or copper salts, potassium oxide, potassium carbonate, oxides of chromium, manganese, aluminum, vanadium, magnesium, thorium and molybdenum. For example, an iron oxide catalyst useful in this invention may contain about 50 to about 95 wt. % iron red as $Fe_2O_3$, about 5 to about 30 wt. % potassium compound, measured as potassium oxide, such as potassium carbonate and potassium oxide and up to about 20 wt. % of other compounds, measured as their oxides, such as compounds of vanadium, cadmium, magnesium, manganese, nickel, rare earths, chromium, and mixtures thereof. Preferable iron oxide-containing catalysts contain about 70 to about 90 wt. % iron oxide (as $Fe_2O_3$) about 5 to about 30 wt. % potassium compound (as $K_2O$) and up to about 20 wt. % other compounds measured as their oxides. One specific example of an iron oxide-containing catalyst suitable for ethylbenzene dehydrogenation contains about 80–90 wt. % iron oxide (as $Fe_2O_3$), about 8–15 wt. % potassium oxide, about 1–3 wt. % chromium oxide and about 0–1 wt. % vanadium oxide.

Compounds which catalyze oxidation of hydrocarbons, such as platinum or palladium salts, should be substantially absent from iron oxide-containing catalysts used in this invention.

Various iron oxide-containing catalysts and processes using such catalysts have been reported widely. Examples of such catalysts and processes include U.S. Pat. Nos. 2,111,726; 2,408,140; 2,414,585; 2,426,829; 2,461,147; 2,870,228; 2,945,960; 3,084,125; 3,179,706; 3,179,707; 3,205,179; 3,291,756; 3,306,942; 3,361,683; 3,387,053; 3,424,808; 3,703,593; 3,849,339; 3,907,416; 4,039,601; 4,143,083; 4,144,197; and 4,152,300, all incorporated by reference herein. Commercially, suitable iron oxide catalysts are sold under trademarks such as Shell-105, Shell-115, Shell-015, UCI-G64D, UCI-G64E, UCI-G64F and UCI-G64I.

Conversion processes using iron oxide-containing catalysts include hydrocarbon dehydrogenation such as ethylbenzene to styrene, ethyltoluene to vinyltoluene, cumene to alpha-methylstyrene and butenes to butadiene. Other conversion processes are formation of gasoline fraction hydrocarbons from synthesis gas, dealkylation of alkylaromatics such as toluene to benzene, and synthesis of ammonia from nitrogen and hydrogen. Broadly, conversion processes using iron oxide-containing catalysts are run at temperatures ranging from about 150° to about 1000° C. at pressure of about 0.01 to about 100 atmospheres (1–10,000 kPa) at liquid hourly space velocities of about 0.01 to about 10 $hr^{-1}$. Conditions for conversion processes using the invention described herein are not altered substantially from conventional processes except in contact of a low level of molecular oxygen to the iron oxide-containing catalyst. Therefore conditions for such conversion reactions are known to the art. For example, in a Fischer-Tropsch reaction using an iron oxide-containing catalyst, a mixture of carbon monoxide and hydrogen reacts to form paraffinic and olefinic hydrocarbons typically at about 150° to about 350° C. at about 1 to 30 atmospheres (100–3000 kPa).

Dehydrogenation processes using iron oxide catalysts are well known. For example, K. K. Kearby in Catalysis Vol. III, P. H. Emmett, editor, Reinhold Publishing Corp., 1955, pp. 453–491, incorporated herein by reference, describes catalytic dehydrogenation processes such as dehydrogenation of ethylbenzene to styrene and butene to butadiene using Shell-105-type iron oxide catalysts.

In a typical dehydrogenation process, hydrocarbon, usually diluted with steam, is contacted with a heterogeneous iron oxide-containing catalyst at about 400° to about 800° C. at a pressure of about 0.05 to about 3 atmospheres (5 to 300 kPa) with a liquid hourly space velocity (LHSV) (defined as the volumetric liquid hydrocarbon feed rate (in cc/hr, corrected to 60° F.) divided by the volume of catalyst) of about 0.05 to about 2 hy$^{-1}$. Suitable conditions for a particular hydrocarbon dehydrogenation are known to the art. In ethylbenzene dehydrogenation to styrene, typical process conditions are about 550° to about 753° C. at about 0.1 to about 2 atmospheres (10 to 200 kPa) and a space velocity of about 0.1 to about 1.5 hr$^{-1}$. Preferable conditions are about 600° to about 680° C., at about 0.3 to about 2 atmospheres (30 to 200 kPa) a space velocity of about 0.2 to about 1.0 and a steam/hydrocarbon mole ratio of about 5 to about 20.

It is observed that iron oxide catalysts used in ethylbenzene dehydrogenation deactivate steadily over time as measured by ethylbenzene conversion. A catalyst can be reactivated periodically by steaming in the substantial absence of hydrocarbon feed, but conversion activity thereafter quickly will decline to approximately the same level expected before steaming. In contrast, incorporation of a catalyst regeneration amount of oxygen, or a precursor thereof, according to this invention will slow the rate cf catalyst deterioration such that the useful life of the catalyst is prolonged substantially. Further benefits of use of such a regeneration amount of oxygen of in ethylbenzene dehydrogenation are the ability to operate at lower (less severe) temperatures which improves selectivity and the ability to increase space velocity which results in more efficient operation.

The following examples and comparative runs demonstrate but do not limit the invention disclosed herein.

COMPARATIVE RUN A

Ethylbenzene dehydrogenation tests were performed in a pilot plant using two 1.94-inch (inside diameter) tubular adiabatic reactors in series. A batch of Shell-105 catalyst, in the form of 150-inch extrudates, nominally containing 88.0 wt. % iron oxide (as $Fe_2O_3$) 9.5 wt. % potassium oxide and 2.5 wt. % chromium oxide, which had been used previously in the pilot plant for 2440 hours, was packed into both reactors to a height of about 29 inches and topped with 30 inches of alumina balls as a preheat zone. The catalyst was steamed in situ for 18 hours at about 590° C. prior to hydrocarbon feed introduction. Superheated steam combined with a preheated hydrocarbon feedstream was introduced into the preheat zone of the first reactor where the feed temperature was adjusted to a target operating condition before contacting the first catalyst bed. The hydrocarbon (HC) feedstream typically contained 93.5 wt. % ethylbenzene, 3 wt. % styrene, 3.5 wt. % toluene and a trace amount of benzene. The effluent from the first reactor was reheated in the preheat zone of the second reactor prior to entering the second catalyst bed. The effluent from the second reactor was condensed in a product recovery section and separated into a hydrogen-rich off-gas stream, liquid hydrocarbon product stream and water. The off-gas stream was metered and analyzed for hydrogen, carbon oxides and $C_1$-$C_3$ light hydrocarbon content by gas chromatography. The liquid hydrocarbon products were analyzed for benzene, toluene, ethylbenzene, styrene and other hydrocarbons boiling above styrene by gas chromatography.

Ethylbenzene (EB) conversion was measured at constant operating conditions for the following 23 days (548 hours) in order to establish catalyst activity decline behavior. The test conditions and EB conversions are shown in Table I. Liquid hourly spaced velocity (LHSV) is defined as the volumetric liquid hydrocarbon feed rate (corrected to 15.6° C.) divided by the total volume of catalyst charged into the two reactors. Catalyst bed inlet temperatures were set at 613° C. for the first reactor and 622° C. for the second reactor. Reactor pressures shown in Table I refer to the pressures at the inlet of the first catalyst bed and the outlet of the second catalyst bed. The percent EB conversion is the overall EB disappearance in two reactor stages divided by the amount of EB in the feedstream and multiplied by 100. Table I shows that EB conversion steadily declined from 55.3 wt. % to 52.0 wt. % in a period of 504 hours, or at an average rate of 0.157 wt. % per day. These data are plotted in FIG. 1.

TABLE I

| Catalyst | | | | |
|---|---|---|---|---|
| Type | Shell-105 | | | |
| Initial Age | 2440 | | | |
| LHSV (hr$^{-1}$) | 0.85–0.87 | | | |
| Steam/hydrocarbon (mole ratio) | 8.1 | | | |
| Catalyst Bed Inlet Temperature (°C.) | | | | |
| Reactor 1 | 613 | | | |
| Reactor 2 | 622 | | | |
| Reactor Pressure (atm.) | | | | |
| Reactor 1 Inlet | 1.65 | | | |
| Reactor 2 Outlet | 1.24 | | | |
| Reaction Time (hours) | 44 | 209 | 428 | 548 |
| EB Conversion (wt. %) | 55.3 | 53.9 | 52.4 | 52.0 |

The Shell-105 catalyst used in Run A was removed from the test reactors after 3570 total hours of use and examined. Screened catalyst was loaded back into the two adiabatic reactors described in Run A to a height of 25 inches and topped with 30 inches of alumina balls as described in Run A. Prior to hydrocarbon feed introduction the catalyst was steamed for 17 hours at 540° C. in a manner similar to that performed in Run A, and then treated with steam generated from distilled water containing 5 wt. % hydrogen peroxide ($H_2O_2$) for two hours followed by the usual steaming without peroxide addition for another hour to remove any residual peroxide in the reactor system. The hydrocarbon feedstock and test procedure were similar to those described in Run A.

After start-up a series of tests was conducted at constant operating conditions to determine catalyst activity and activity maintenance by measuring EB conversions with and without hydrogen peroxide addition. The test conditions and results are summarized in Table II. At 20 hours after start-up the Shell-105 catalyst gave 57.3 wt. % EB conversion. For the test period beginning with 24 hours after start-up and ending at 212 hours after start-up, hydrogen peroxide ($H_2O_2$) was continuously added to the water feed in concentrations of 150–480 ppm. Superheated steam was generated from this water containing hydrogen peroxide and, after combined with the hydrocarbon feedstream, fed to the first reactor. The hydrogen peroxide concentrations of 150–480 ppm based on water feed were equivalent to 0.00032–0.00103 moles of oxygen ($O_2$) per mole of hydrocarbon feed. Unexpectedly, very little decline in EB conversion was obtained during the 24-212 hour period where hydrogen peroxide was added to the water feed. When hydrogen peroxide addition was stopped for the next period covering between 212 hours and 405 hours after start-up, EB conversion rapidly declined from 56.8 wt. % to 54.4 wt. % at an average rate of 0.298 wt. % per day in comparison with 0.043 wt. % per day for the previous test period. The addition of hydrogen peroxide was resumed at 405 hours after start-up and continued until 735 hours after start-up in the amounts of 100-200 ppm based on water feed or equivalent to $0.21 \times 10^{-3}$ to $0.43 \times 10^{-3}$ moles of oxygen per mole of hydrocarbon feed. The resumption of hydrogen peroxide addition in this test period resulted in a slowdown of EB conversion decline rate to 0.065 wt. % per day from the preceding period, 0.298 wt. % per day without peroxide addition. The data are plotted in FIG. 1.

Since peroxide was not detected in the effluents of the first or second catalyst bed by titration with potassium dichromate, all peroxide appears to have decomposed to oxygen and water. Further, the improved performance of the catalyst shown using peroxide in Table II may be due only to improvement in the first reactor catalyst.

TABLE II

| Catalyst | | | | |
|---|---|---|---|---|
| Type | Shell-105 | | | |
| Initial Age (hours) | 3570 | | | |
| LHSV ($hr^{-1}$) | 0.81-0.82 | | | |
| Steam/hydrocarbon (mole ratio) | 8.1 | | | |
| Catalyst Bed Inlet Temperature (°C.) | | | | |
| Reactor 1 | 613 | | | |
| Reactor 2 | 622 | | | |
| Reactor Pressure (atm.) | | | | |
| Reactor 1 Inlet | 1.58 | | | |
| Reactor 2 Outlet | 1.27 | | | |
| Reaction time (hours) | 0-24 | 24-212 | 212-405 | 405-735 |
| $H_2O_2$ in Steam (ppm) | 0 | 150-480 | 0 | 100-200 |
| Equivalent $O_2/HC$ (mole ratio $\times 10^3$) | 0 | .32-1.03 | 0 | .21-0.43 |
| EB Conversion Decline (wt. %/day) | — | 0.043 | 0.298 | 0.065 |
| Reaction Time (hours) | 20 | 43 | 212 | 405 | 735 |
| EB Conversion (wt. %) | 57.3 | 57.1 | 56.8 | 54.4 | 53.5 |

The data presented in Run A and Example I as illustrated in FIG. 1 demonstrate the beneficial effects of very low levels of oxygen addition to an ethylbenzene dehydrogenation process using an iron oxide-containing catalyst system. In both experiments the steam/hydrocarbon ratio, which is considered the most critical variable effecting conversion rate decline over time, was identical. The catalyst in Example I showed a higher initial conversion than that in Run A probably due to peroxide treatment used prior to introduction of hydrocarbon feed. Such high conversion level in Example I would have declined rapidly. However, addition of peroxide to the process steam (i.e., addition of in situ-formed molecular oxygen to the catalyst) maintained a higher conversion level than observed in Run A.

As shown in FIG. 1, catalyst activity declined rapidly and steadily over time without peroxide or oxygen addition. In Example I, during addition of peroxide (24-480 hours and 405-735 hours) the rate of catalyst activity decline was slow compared to the time (212-405 hours) in which no peroxide was added. The rate of decline in the period (212-405 hours) of Example I during which peroxide was not added is greater than the rate of catalyst activity decline observed in Comparative Run A in which peroxide was never added. It is believed that if peroxide addition were not resumed at 405 hours catalyst activity would have declined rapidly to the level observed in Run A. It is concluded that addition of peroxide (a precursor of molecular oxygen) caused a substantial decrease in the rate of catalyst activity decline over time.

EXAMPLE II

Figure 2:
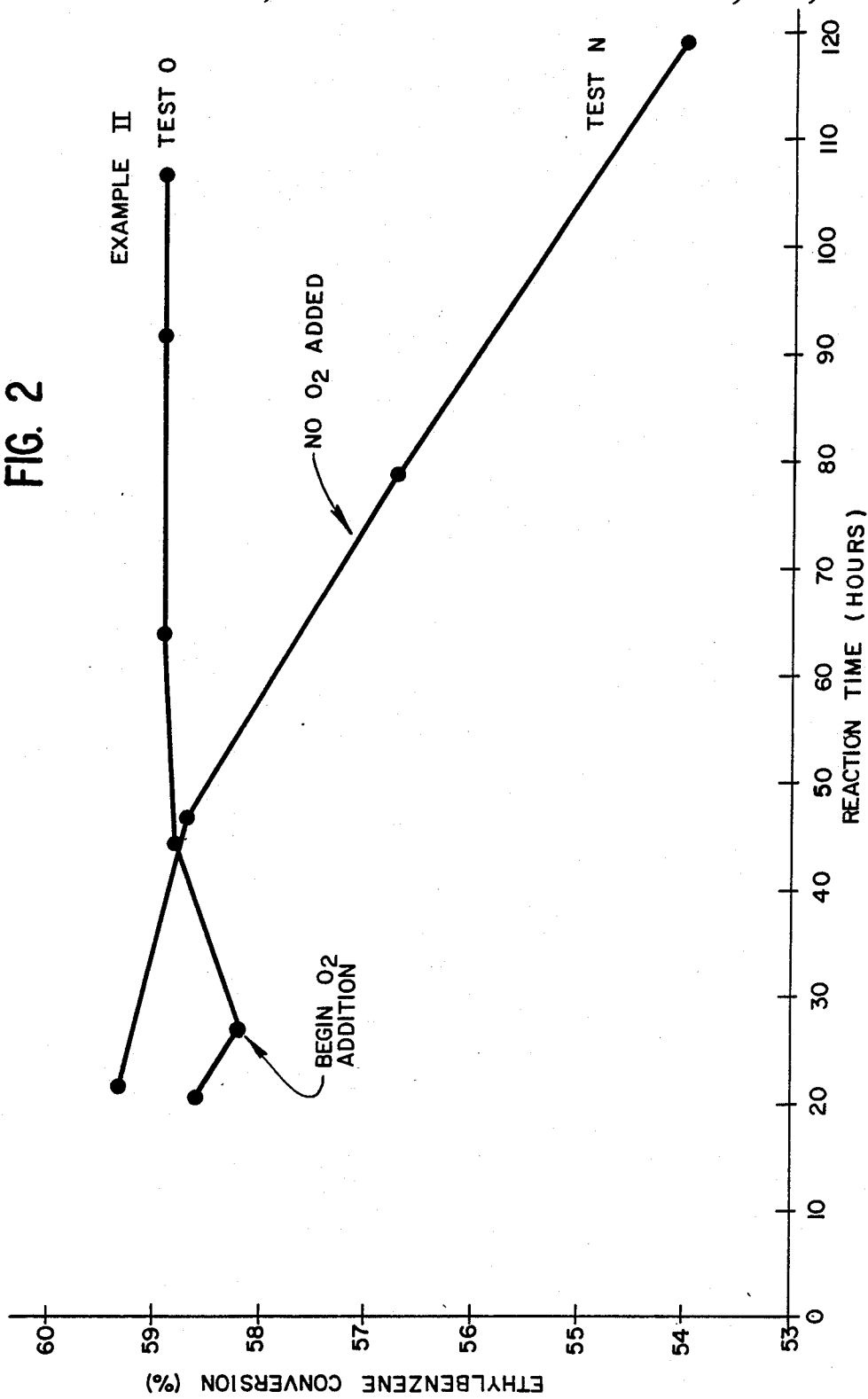
FIG. 2 illustrates data from Example II showing the effect of oxygen addition to feedstreams in an ethylbenzene dehydrogenation process on ethylbenzene conversion as a function of time.

The effect of oxygen addition on ethylbenzene dehydrogenation catalyst performance was tested using the same pilot plant as described and used in Run A and Example I; however, a 6/1 steam/hydrocarbon mole ratio, a severe condition for maintaining catalyst activity, was used. Ethylbenzene dehydrogenation using aged Shell-105 catalyst was performed with and without oxygen addition to the catalyst beds. The test performed without oxygen addition is designated Test N while the test performed with oxygen addition is designated Test O. In both tests a 25-inch bed of Shell-105 catalyst was loaded into each of the two pilot plant reactors and steamed for three hours at 560° C. prior to introduction of hydrocarbon feed. Test N preceded Test 0 with the same batch of Shell-105 catalyst. Air was used as a source of oxygen for Test O. Air was added to the steam-hydrocarbon mixture at the inlet side of each reactor which was located in the preheat zone ahead of the catalyst bed. Results from Tests N and 0 are shown in Table III and FIG. 2. The oxygen to hydrocarbon mole ratios shown in Table III for both the first and the second reactor were based on the hydrocarbon feed to the first reactor.

A comparison of Tests N and O show that ethylbenzene conversion declined very rapidly at a 6/1 steam/hydrocarbon ratio without oxygen addition (Test N), while ethylbenzene conversion did not decline to any appreciable extent while oxygen was added (Test O). In fact the data show an increase in ethylbenzene conversion after addition of low levels of oxygen.

Styrene selectivity, defined as the net styrene production per net weight change of ethylbenzene from feed to product, is an important aspect of catalyst performance. Typically, styrene selectivities decrease with increasing ethylbenzene conversion as is observed in Test N and, therefore, usually are compared at constant conversion. Styrene selectivity at a given conversion could deteriorate with deteriorating catalyst performance. Test O shows that addition of oxygen to each reactor in the range of $1.6 \times 10^{-3}$ to $3 \times 10^{-3}$ moles $O_2$/mole of hydrocarbon did not cause any penalty in styrene selectivity. The styrene selectivities obtained during the period of oxygen addition were practically equal to the initial selectivity obtained without oxygen at the beginning of Test O, or even greater than the selectivity shown in Test N when compared at the same conversion.

TABLE III

| Catalyst | Test N | Test O |
|---|---|---|
| Type | Shell-105 | Shell-105 |
| Initial Age (hours) | 4780 | 5600 |
| LHSV ($hr^{-1}$) | 0.82 | 0.82 |
| Steam/hydrocarbon (mole ratio) | 6.0 | 6.0 |
| Catalyst Bed Inlet Temperature (°C.) | | |

TABLE III-continued

| | | |
|---|---|---|
| Reactor 1 | 632 | 629 |
| Reactor 2 | 639 | 644 |
| Reactor Pressure (atmos.) | | |
| Reactor 1 Inlet | 1.58 | 1.58 |
| Reactor 2 Outlet | 1.27 | 1.27 |

| | $O_2/HC$ mole ratio $\times 10^3$ | | Ethylbenzene Conversion (%) | Styrene Selectivity (wt. %) |
|---|---|---|---|---|
| Reaction Time (hours) | Reactor 1 | Reactor 2 | | |
| Test N | | | | |
| 22 | 0 | 0 | 59.3 | 86.2 |
| 47 | 0 | 0 | 58.7 | 86.2 |
| 79 | 0 | 0 | 56.7 | 87.4 |
| 119 | 0 | 0 | 54.0 | 89.2 |
| Test O | | | | |
| 21 | 0 | 0 | 58.6 | 87.6 |
| 27 | 1.62 | 1.98 | 58.2 | 87.7 |
| 44 | 1.61 | 1.97 | 58.8 | 87.5 |
| 64 | 2.96 | 2.27 | 58.9 | 87.6 |
| 92 | 3.00 | 2.08 | 58.9 | 87.6 |
| 107 | 3.00 | 3.00 | 58.9 | 87.7 |

COMPARATIVE RUN B

Using reaction conditions similar to those described in Run A, hydrogen peroxide was added to the two adiabatic reactors in the ethylbenzene dehydrogenation pilot plant in which Shell-105 catalyst was in place. The amounts of equivalent moles of oxygen per mole of hydrocarbon added to the first and second reactors were 0.01 and 0.047, respectively. These amounts were about one order of magnitude higher than the amounts of oxygen used in Examples I and II. Immediately after the peroxide addition, the reactor temperatures rose uncontrollably indicating exothermic oxidation reactions with hydrocarbons as well as hydrogen. Even 30 minutes after the peroxide addition was stopped, the catalyst bed temperatures remained higher than before the peroxide injection; the first catalyst bed inlet was 11° C. higher; the second catalyst bed inlet was 25° C. higher at 666° C., and the second bed outlet was 15° C. higher than the base temperature before the peroxide addition. This experiment indicates the amount of peroxide added was excessive which caused a temperature control problem as well as burning of hydrocarbons.

COMPARATIVE RUN C

Ethylbenzene was dehydrogenated in two adiabatic reactor stages each filled with 30 inches of Shell-105 catalyst. Air was added to the interstage, i.e., to the second reactor inlet in an amount equivalent to 0.054 moles of oxygen per mole of ethylbenzene feed, which was approximately ten times as much as the air used in Example II. Because of the relatively large quantity of air addition the temperatures throughout the second reactor became hotter than the temperature profile normally established for a base case without air addition. By reducing heat duty of the preheat zone of the second reactor, the inlet temperature of the second catalyst bed was set at the same temperature as that of the base case without air addition.

The results obtained with and without the interstage air addition were compared at the same testing conditions. The inlet temperatures to the first and the second catalyst bed were respectively 646° C. and 636° C. However, the second catalyst bed outlet temperature was still 2° C. higher for the case with air addition than without, 604° C. vs 602° C. Reactor pressures were 1.73 atmospheres at the inlet of the first catalyst bed and 1.25 atmospheres at the outlet of the second catalyst bed. Hydrocarbon liquid hourly space velocity was 0.74 cc of EB/hr/cc of catalyst and steam/HC mole ratio was 10/1. Pure ethylbenzene was used as the feed in both tests. The overall two-stage results obtained with the interstage air addition were 50.9 wt. % EB conversion and 90.5 wt. % styrene selectivity whereas the results without air addition, although obtained two days later than the former, were 52.0 wt. % EB conversion and 90.8 wt. % styrene selectivity. The interstage air addition at the rate of 0.054 moles of $O_2$/mole of HC gave a lower EB conversion along with a lower styrene selectivity than the case without air addition. Contrary to the expectation of a higher selectivity at lower conversion, styrene selectivity shown for the interstage air addition, 90.5 wt. % at 50.9 wt. % EB conversion, was lower than 90.8 wt. % selectivity obtained without air addition at 52.0 wt. % conversion.

Run C indicates addition of relatively too much air, such as 0.05 moles of $O_2$/mole of HC, harms the catalyst in terms of conversion drop and styrene selectivity losses, while a small quantity of air addition such as 0.0002–0.006 moles of $O_2$/mole of HC would have beneficial effects as exemplified in Example I and Example II.

In summary, addition of small amounts of oxygen improves catalyst activity maintenance without loss of styrene selectivity. However, too much oxygen addition beyond a certain range of $O_2/HC$ mole ratio can cause burning of valuable aromatic hydrocarbons, styrene selectivity losses and other adverse effects on catalyst performance.

What is claimed is:

1. A conversion process wherein an alkylaromatic compound is dealkylated using an iron oxide-containing catalyst contacting such catalyst with a feed containing about 0.0001 to about 0.01 mole of oxygen per mole of feed in the substantial absence of an oxidation catalyst whereby the life of said iron oxide-containing catalyst is extended.

2. The process of claim 1 wherein toluene is dealkylated to benzene.

* * * * *

UNITED STATES PATENT OFFICE
CERTIFICATE OF CORRECTION

Patent No. 4,902,845  Dated February 20, 1990

Inventor(s) Dae K. Kim and George A. McConaghy

It is certified that error appears in the above-identified patent and that said Letters Patent is hereby corrected as shown below:

| Patent Column | Line | |
|---|---|---|
| 1 | 23 | reads "hydrogen As" and should read --hydrogen. As-- |
| 2 | 49 | reads "The hydrocarbon" and should read --Other hydrocarbon-- |
| 4 | 6-7 | reads "iron red as" and should read --iron oxide measured as-- |
| 5 | 11 | reads "hy$^{-1}$" and should read --hr$^{-1}$-- |
| 5 | 33 | reads "oxygen of in ethylbenzene" and should read --oxygen in ethylbenzene-- |
| 5 | 44 | reads "150-inch" and should read --1/8-inch-- |
| 5 | 55-56 | reads "hydrocarbon carbon (HC)" and should read --hydrocarbon (HC)-- |

Signed and Sealed this

Twelfth Day of November, 1991

*Attest:*

HARRY F. MANBECK, JR.

*Attesting Officer*  *Commissioner of Patents and Trademarks*